US006849720B2

(12) United States Patent
Yonah et al.

(10) Patent No.: US 6,849,720 B2
(45) Date of Patent: Feb. 1, 2005

(54) MONOCLONAL ANTIBODIES TO THE HUMAN LDL RECEPTOR, THEIR PRODUCTION AND USE

(75) Inventors: Nachum Yonah, Gedera (IL); Dany Suissa, Rehovot (IL); Ilana Belzer, Rishon le Zion (IL); Francesco Antonetti, Rome (IT); Moshe Smolarsky, Rehovot (IL); Michel Dreano, Collonges-sous-Saleve (FR)

(73) Assignee: Applied Research Systems ARS Holding N.V., Curacao (NL)

( * ) Notice: Subject to any disclaimer, the term of this patent is extended or adjusted under 35 U.S.C. 154(b) by 0 days.

(21) Appl. No.: 10/221,679

(22) PCT Filed: Mar. 8, 2001

(86) PCT No.: PCT/IL01/00216

§ 371 (c)(1),
(2), (4) Date: Jan. 15, 2003

(87) PCT Pub. No.: WO01/68710

PCT Pub. Date: Sep. 20, 2001

(65) Prior Publication Data

US 2003/0186343 A1 Oct. 2, 2003

(30) Foreign Application Priority Data

Mar. 13, 2000 (IL) .................................................. 135025
Oct. 23, 2000 (IL) .................................................. 139217

(51) Int. Cl.$^7$ ...................... A61K 39/395; C07K 16/28; C12Q 1/70
(52) U.S. Cl. .............................. 530/388.22; 424/143.1; 435/5; 435/7.21; 435/70.21; 435/452; 435/332; 435/334; 436/518; 436/548; 436/820; 530/413
(58) Field of Search .................. 435/5, 7.21, 7.94, 435/70.21, 452, 328, 332, 334; 436/518, 548, 820; 424/143.1, 172.1; 514/2; 530/388.22, 387.2, 387.3, 413

(56) References Cited

U.S. PATENT DOCUMENTS 5,723,438 A * 3/1998 Rubinstein et al. ............ 514/2

OTHER PUBLICATIONS van Driel et al., 1989. Stoichiometric binding of low density lipoprotein (LDL) and monoclonal antibodies to LDL receptors in a solid phase assay. J. Biol. Chem. 264(16): 9533–9538.*

Xie Chong–lun et al., 1991. Preparation and properties of monoclonal antibodies against low density lipoprotein (LDL) receptors. Acta Biochim. Biophys. Sinica 23(3): 189–195.*

Agnello et al., 1999. Hepatitis C virus and otehe Flaviviridae viruses enter cells via low density lipoprotein receptor. PNAS 96(22): 12766–12771.*

Caruso et al., 1993. Demonstration of low density lipoprotein receptor in human colonic carcinoma ans surrounding mucosa by immunoenzymatic assay. Ital. J. Gastroenterol. 25: 361–367.*

Owens et al., 1994. The genetic engineering of monoclonal antibodies. J. Immunolog. Meth. 168: 149–165.*

Hay et al., eds., 1992. American Type Culture Collection Catalogue of Cell Lines and Hybridomas. Seventh Edition, 1992. American Type Culture Collection, Rockville. p. 346.*

* cited by examiner

Primary Examiner—Christopher L. Chin
Assistant Examiner—James L. Grun
(74) Attorney, Agent, or Firm—Browdy and Neimark

(57) ABSTRACT

There are provided monoclonal antibodies to the LDL receptor which are useful for the identification and purification of LDL and in treatment of e.g. hepatitis C infection.

13 Claims, 3 Drawing Sheets

MONOCLONAL ANTIBODIES TO THE HUMAN LDL RECEPTOR, THEIR PRODUCTION AND USE

FIELD OF THE INVENTION

The present invention relates to monoclonal antibodies which specifically recognise the human receptor for low-density lipoproteins (LDLR). These antibodies are useful e.g. for the identification and purification of human soluble LDLR (hsLDLR) in production processes as well as in the identification and treatment of diseases such as, hepatitis C infection (HCV).

BACKGROUND OF THE INVENTION

Cholesterol, a component of all eukaryotic plasma membranes, is essential for the growth and viability of cells in higher organisms. However, high serum levels of cholesterol cause disease and death by contributing to the formation of atherosclerotic plaques in arteries throughout the body. The major site of cholesterol synthesis in mammals is the liver. Appreciable amounts of cholesterol are also formed by the intestine. The rate of cholesterol formation by these organs is highly responsive to the amount of cholesterol absorbed from dietary sources. Cells outside of the liver and intestine acquire cholesterol from the plasma rather than by synthesising it de novo. Cholesterol and other lipids are transported in body fluids by lipoproteins, which are classified according to increasing density. A lipoprotein is a particle consisting of a core of hydrophobic lipids surrounded by a shell of polar lipids and apoproteins. These lipoproteins have two roles: they solubilize highly hydrophobic lipids and they contain signals that regulate the movement of particular lipids in and out of specific target cells and tissues. Cholesterol is transported in body fluids by low-density lipoproteins (LDL) which binds to a specific receptor on the plasma membrane of non hepatic cells. The receptor-LDL complex is then internalised into the cells by a transport mechanism known as receptor mediated endocytosis (Goldstein et al. 1979). The low density lipoprotein (LDL) receptor is the prototype of a family of structurally related cell surface receptors that mediate endocytosis of multiple ligands in mammalian cells.

The LDL receptor consists of 822 amino acid residues and exhibits a molecular weight of 164000. It is composed of several domains some of which share sequence homology with other proteins. Its $NH_2$-terminal ligand-binding domain consists of 292 residues, arranged in 7 cysteine-rich imperfect repeats. Each repeat contains six cysteine residues which are disulphide bonded in the pattern one to three, two to five, and four to six. (Bieri et al. 1995). This domain is followed by four additional domains: the first consists of 400 amino acid residues and is homologous to the EGF receptor, the second consists of 58 amino acid residues rich in O-linked sugars, the third is a single trans-membrane domain of 22 amino acid residues and the fourth is a cytoplasmic domain of 50 amino acid residues (Sudhof et al. 1985), (Brown et al. 1986).

The physiologic importance of the LDL receptor was revealed by Brown and Goldstein's studies on familial hypercholesterolemia (FH). The disease was found to be due to a molecular genetic defect resulting in the absence or deficiency of functional receptors for LDL (Brown et al. 1976). Several classes of FH mutations have been characterised. (Goldstein et al. 1975).

A soluble form of the sLDLR exhibiting antiviral activity was identified and isolated from the culture supernatant of interferon-induced cells (Fischer et al. 1993) and in body fluids (Fischer et al. 1994). Several interferon-induced proteins have been identified that are instrumental in the induction of the antiviral state by IFNs. One such protein exhibiting antiviral activity was produced and accumulated in the culture supernatant of human amnion WISH cells. This protein was purified to homogeneity and identified as the sLDLR (see EP 0 553 667 and Fischer et al. 1993). The sLDLR was found to be secreted into the medium by mammalian cells that enter an antiviral state in response to interferon. In contrast to interferon, sLDLR does not induce an antiviral state in the cells but is antiviral by itself. It was found that sLDLR apparently has to be present throughout the process of viral replication maturation and budding suggesting it might be involved in a complex process that leads to the inhibition of virus assembly or budding (unpublished data). Endocytosis of the hepatitis C virus has been recently shown to be mediated by LDL receptors on cultured cells (Agnello et al. 1999). These and other findings suggest that the family of LDL receptors may serve as viral receptors. Therefore, antibodies rised against the sLDLR receptor may block the entry and budding of viral particles by binding to the cellular LDL receptor.

The only available monoclonal antibody to LDLR known so far is C7, an antibody to bovine LDLR (Beisiegel et al. 1981, commercially available from Amersham, UK) which was prepared by immunization of mice with the bovine adrenal cortex LDLR purified to homogeneity. Membranes from the bovine adrenal cortex were solubilized and the receptor was partially purified by elution from a DEAE-cellulose column (Beisiegel et al. 1981). The antibody to the bovine LDLR only weakly cross-reacts with human LDLR.

In fact, the C7 Mab to bovine LDLR was found to have significant disadvantages when used for detection and quantitation of recombinant human LDLR:

a) It has very low affinity to the human LDLR
b) It significantly cross reacts with cell culture derived impurities Specific antibodies to human LDLR were not previously available. This appears surprising since it is very common to raise antibodies against novel proteins, be it for purification, identification or for assay development purposes. It is possible that such antibodies have not been generated so far, since a condition for generating monoclonal antibodies is the availability of sufficiently large amounts of highly purified antigen which allow efficient immunization of mice. A highly purified antigen is one which appears as a single major peak in RP-HPLC. Furthermore methods for identification and quantitation of the antigen during purification processes were not easy to establish. In accordance with the invention, the antiviral activity assay described herein was employed for the identification of LDLR during purification processes.

There exists a need to generate specific Mabs to human soluble LDLR to provide the means for developing an efficient immunoassay (ELISA) and for the identification of the protein in Western blot. These antibodies are required for the monitoring and quantitation of the recombinant human soluble LDLR during development of the production and purification processes of the recombinant protein and for detection of the natural protein.

SUMMARY OF THE INVENTION

The present invention allows the generation of hybridoma cells lines producing monoclonal antibodies capable of specifically recognising and binding the human LDL receptor and fragments thereof.

More specifically the present invention allows the generation of hybridoma cells lines producing monoclonal antibodies capable of specifically recognising and binding the human soluble LDL receptor.

Thus the present invention relates to a monoclonal antibody, chimeric antibody, humanized antibody, anti-anti-Id antibody or fragment thereof which specifically recognises and binds the human LDL receptor and fragments thereof, except monoclonal antibody C7.

The present invention provides such monoclonal antibodies that recognise and bind the human soluble LDLR and meet the following needs:

1. Mabs that can be used as a pair in an ELISA, e.g. a sandwich ELISA (Enzyme Linked Immuno Sorbent Assay) for detection of human soluble LDLR.
2. Mabs that can be used for identification of the LDLR in Western Blot analysis.
3. Mabs that can be used to neutralise the antiviral biological activity of the human soluble LDLR.
4. Mabs that can be used to inhibit virus infection, such as HCV.

The present invention further provides a method for the detection and/or the quantitation of human LDLR which comprises the use of the specific monoclonal antibodies according to the invention in a known manner for that purpose.

The present invention also provides cloned hybridoma comprising a spleen cell from a mammal immunized with recombinant human LDLR and a homogenic or heterogenic lymphoid cell.

A monoclonal antibody according to the invention is prepared in a conventional manner, e.g. by growing a cloned hybridoma comprising a spleen cell from a mammal immunized with hsLDL and a homogenic or heterogenic lymphoid cell in liquid medium or mammalian abdomen to allow the hybridoma to produce and accumulate the monoclonal antibody.

The invention, in yet another aspect, provides a method for purifying the human LDLR which comprises contacting a material containing crude LDLR with a monoclonal antibody according to the invention. A column with adsorbed LDLR specific monoclonal antibody may be used as an affinity purification step, in the purification process of the recombinant protein.

A method for detecting and measuring recombinant human LDLR which comprises using as antibody the monoclonal antibodies of the present invention in an ELISA assay as described in example 5.

As the LDLR or fragment of a LDLR for immunizing animals any LDLR can be used as long as it is the LDLR of a warm-blooded mammal. A mutein of LDLR can be also used. A representative example of such a mammalian human soluble LDLR is the soluble LDLR +291 form which includes the amino acid sequence beginning at amino acid Asp at position +4 and ending with amino acid Glu at position +291 of the sequence of the human LDLR, any other form may be used as well, such as the +292 form etc.

+SP: positive-strand RNA assay; −SP: negative-strand RNA assay; X: blank.

DETAILED DESCRIPTION OF THE INVENTION

Monoclonal antibodies (Mabs) to human soluble LDLR (hsLDLR) were generated. Using these monoclonal antibodies, an ELISA and a Western blotting procedure for the identification of hsLDLR and a neutralising assay to the antiviral activity of hsLDLR were developed.

The Mabs were generated in mice, immunized with the recombinant +291 form of hsLDLR, which consists of the N-terminal ligand binding domain of the human soluble LDLR, from Asp +4 to Glu +291. The recombinant +291 form of hsLDLR, was produced in CHO cells and purified to homogeneity.

The immunized mice produced significant titres of specific antibodies. After screening of hybridomas, five clones (numbers 12, 28, 29, 30 and 50) were identified as the highest antibody producers. These clones were selected for further subcloning. After subcloning, 29 subclones which had high antibody productivity were isolated and ampoules from the parent clones and from the subclones were frozen.

A pair of monoclonal antibodies was chosen for the ELISA to the r-hsLDLR. Mab 28 was selected as the coating antibody, and Mab 29.8, labelled with biotin, was chosen as the second antibody. Mabs 12.6 and 29.8 were found to be suitable for the identification of the native and recombinant hsLDLR in Western blot analysis and Mabs 28 and 30 were found to be suitable for the identification of the recombinant hsLDLR in Western blot analysis. Mabs 12.6 and 50.30 were found to be suitable for inhibiting the antiviral activity of hsLDLR.

Figure 3:
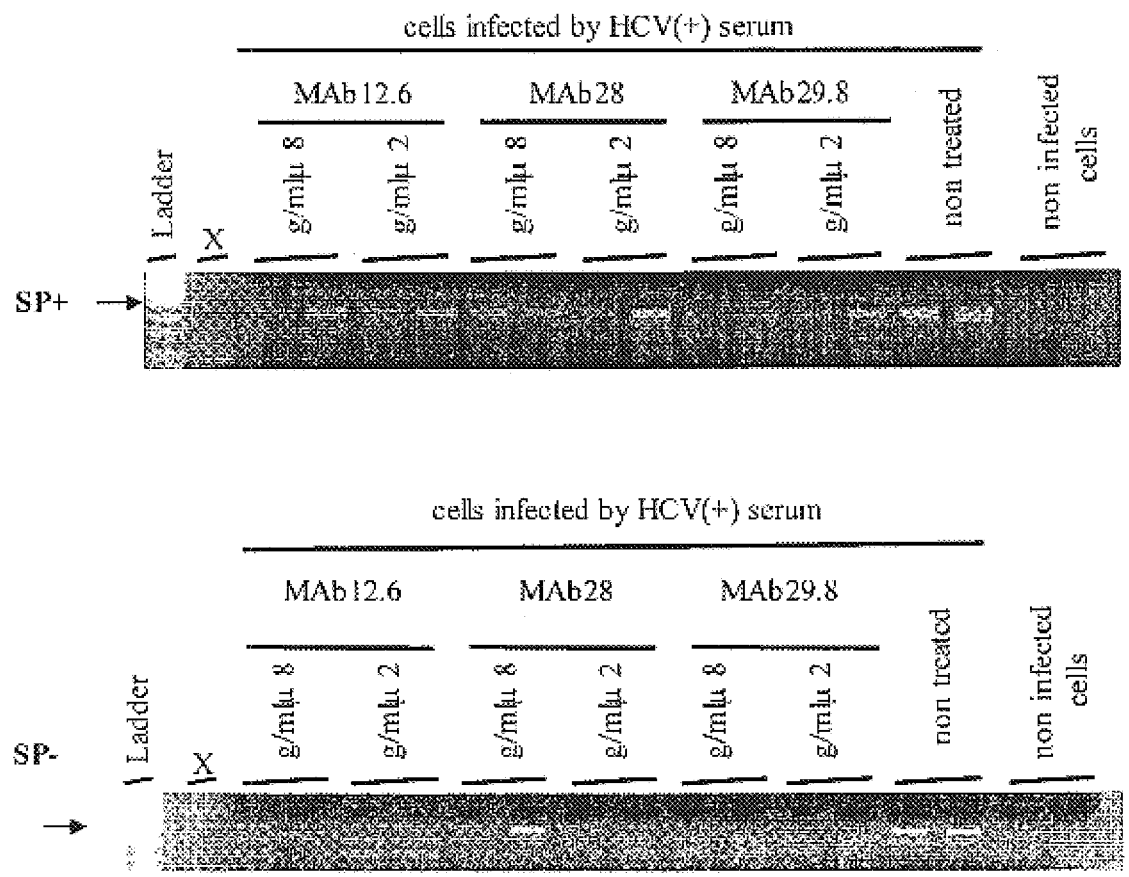
FIG. 3 shows the effects of Mabs 12.6, 28 and 29.8 on the production of HCV(+) and (−) strands in culture FT167. Cells were treated 30 minutes before infection with MAb anti-LDLR (8 or 2 µg/ml). Then, cells were infected overnight with 25 µl of HCV(+) serum (N° 42;1b). The day after Infection, three washes were performed and new medium was added and changed every 48 hours. Five days after infection, the hepatocytes were harvested, RNA was purified and 1 µg cellular RNA was analyzed by rTth RT-PCR (Perkin Elmer). Assays were performed in duplicate.

It was also found in accordance with the invention that Mabs 12.6, 28 and 29.8 inhibit replication of the viral genome of hepatitis C virus (HCV) in human hepatocytes primary cultures. Thus, these antibodies may be used for the treatment of hepatitis C infection (FIG. 3).

The subclass isotype of the Mab produced by the clones was determined. Clones 12.6, 28, 29.8 and 30 were identified as $IgG_1$ whereas clone 50.30 was found to be IgM.

The Mabs, developed against the +291 form of the hsLDLR recognised also other forms of the hsLDLR, i.e. the +292 form and the +331 form of the r-hsLDLR produced in recombinant CHO cells, in ELISA and in Western blot analysis. The +292 form comprises the N-terminus part of the receptor from amino acid residue Asp +4 to Cys +292 and the +331 form comprises the N-terminus part of the receptor from amino acid residue Asp +4 to Cys +331.

The antigen used to immunize mice for generating monoclonal antibodies was the r-hsLDLR +291 form, which was produced in CHO cells. Production of the r-hsLDLR was performed in bioreactors, using the stationary phase Fibracel matrix system. The r-hsLDLR was purified to homogeneity and used for immunizing mice.

Immune spleen cells from the best mouse responder were used for fusion and generation of hybridomas.

As regards the antibodies mentioned herein throughout, the term "monoclonal antibody" is meant to include monoclonal antibodies, chimeric antibodies, fully humanized antibodies, antibodies to anti-idiotypic antibodies (anti-anti-Id antibody) that can be labeled in soluble or bound form, as well as fragments thereof provided by any known technique, such as, but not limited to enzymatic cleavage, peptide synthesis or recombinant techniques.

A monoclonal antibody contains a substantially homogeneous population of antibodies specific to antigens, which populations contains substantially similar epitope binding sites. Mabs may be obtained by methods known to those skilled in the art. See, for example Kohler and Milstein, Nature, 256:495–497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992–1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of Mabs in vivo or in situ makes this the presently preferred method of production.

Chimeric antibodies are molecules of which different portions are derived from different animal species, such as those having the variable region derived from a murine Mab and a human immunoglobulin constant region. Chimeric antibodies are primarily used to reduce immunogenicity in application and to increase yields in production, for example, where murine Mabs have higher yields from hybridomas but higher immunogenicity in humans, such that human/murine chimeric Mabs are used. Chimeric antibodies and methods for their production are known in the art (Cabilly et al., Proc. Natl. Acad. Sci. USA 81:3273–3277 (1984); Morrison et al., Proc. Natl. Acad. Sci. USA 81:6851–6855 (1984); Boulianne et al., Nature 312:643–646 (1984); Cabilly et al., European Patent Application 125023 (published Nov. 14, 1984); Neuberger et al., Nature 314:268–270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., J. Immunol. 137:1066–1074 (1986); Robinson et al., International Patent Application No. WO8702671 (published May 7, 1987); Liu et al., Proc. Natl. Acad. Sci USA 84:3439–3443 (1987); Sun et al., Proc. Natl. Acad. Sci USA 84:214–218 (1987); Better et al., Science 240:1041–1043 (1988); Riechmann et al., Nature 332:323–327. and Harlow and Lane, ANTIBODIES: A LABORATORY MANUAL, supra. These references are entirely incorporated herein by reference.

"Fully humanized antibodies" are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunisation with antigen.

Fully humanized antibodies and methods for their production are known in the art (Mendez et al., Nature Genetics 15:146–156 (1997);Buggemann et al., Eur. J. Immunol. 21:1323–1326 (1991); Tomizuka et al., Proc. Natl. Acad Sci. USA 97:722–727 (2000) Patent WO 98/24893.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the Mab to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original Mab, which induced the anti-Id. Thus, by using antibodies to the idiotypic determinants of a Mab, it is possible to identify other clones expressing antibodies of identical specificity.

Accordingly, Mabs generated against LDLR, its isoforms, analogs, fragments or derivatives of the present invention may be used to induce anti-Id antibodies in suitable animals, such as BALB/c mice. Spleen cells from such immunized mice are used to produce anti-Id hybridomas secreting anti-Id Mabs. Further, the anti-Id Mabs can be coupled to a carrier such as keyhole limpet hemocyanin (KLH) and used to immunize additional BALB/c mice. Sera from these mice will contain anti-anti-Id antibodies that have the binding properties of the original Mab specific for an epitope of the above LDLR protein, or analogs, fragments and derivatives thereof.

The anti-Id Mabs thus have their own idiotypic epitopes, or "idiotopes" structurally similar to the epitope being evaluated. The term "monoclonal antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., J. Nucl. Med. 24:316–325 (1983)).

It will be appreciated that Fab and F(ab')2 and other fragments of the antibodies useful in the present invention may be used for the detection and quantitation of the LDLR protein according to the methods disclosed herein for intact antibody molecules. Such fragments are typically produced by proteolytic cleavage, using enzymes such as papain (to produce Fab fragments) or pepsin (to produce F(ab')2 fragments).

A monoclonal antibody is said to be "capable of binding" a molecule if it is capable of specifically reacting with the molecule to thereby bind the molecule to the antibody. The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody, which antigen is additionally capable of inducing an animal to produce antibody capable of binding to an epitope of that antigen. An antigen may have one or more than one epitope. The specific reaction referred to above is meant to indicate that the antigen will react, in a highly selective manner, with an epitope on its corresponding antibody and not with the multitude of other antibodies which may be evoked by other antigens.

The antibodies, including fragments of antibodies, useful in the present invention may be used to quantitatively or qualitatively detect the LDLR proteins in a sample or to detect presence of cells that express the LDLR proteins of the present invention. This can be accomplished by immunofluorescence techniques employing a fluorescently labeled antibody (see below) coupled with fluorescence microscopy, flow cytometric, or fluorometric detection.

The antibodies (or fragments thereof) useful in the present invention may be employed histologically, as in immunofluorescence or immunoelectron microscopy, for in situ detection of the LDLR proteins of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the LDLR proteins but also its distribution on the examined tissue. Using the present invention, those of ordinary skill will readily perceive that any of wide variety of histological methods (such as staining procedures) can be modified in order to achieve such in situ detection.

Such assays for the LDLR proteins of the present invention typically comprises incubating a biological sample, such as a biological fluid, a tissue extract, freshly harvested cells such as lymphocytes or leukocytes, or cells which have been incubated in tissue culture, in the presence of a labeled antibody capable of identifying the LDLR proteins, and detecting the antibody by any of a number of techniques well known in the art.

The biological sample may be coupled to a solid phase support or carrier such as nitrocellulose, or other solid support or carrier which is capable of immobilizing cells, cell particles or soluble proteins. The support or carrier may then be washed with suitable buffers followed by treatment with a labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well-known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholin-esterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined, as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The invention will be now illustrated by the following non-limiting examples.

EXAMPLES

Example 1

Preparation of CHO r-hsLDLR

Stable recombinant CHO cells expressing human soluble LDLR were generated by co-transfection of CHO-DUKX cells lacking the dihydrofolate reductase (DHFR) gene (Urlaub, G. et al., 1980) with two expression vectors: psLDLR01 containing the N-terminal ligand-binding domain of the LDLR, beginning at amino acid residue Asp (+4) up to Glu 291 (+291), and pDHFR, containing the murine gene for DHFR, both controlled by the promoter and transcription termination elements of the SV40 early region. Transfection was performed by cationic liposomes using LipofectAmine (Gibco BRL), according to the protocol described by the manufacturer. Seventy-two hours after transfection cells were transferred to a selective medium lacking deoxy and ribonucleosides and supplemented with 10% dialysed FCS. Cells expressing DHFR activity were able to form colonies, which were isolated by lifting the cells with trypsin-soaked paper discs The cells were grown and screened for r-hsLDLR activity. The transfected cells were then subjected to gene amplification by MTX, followed by subcloning and selection of the stable producer clones.

r-hsLDLR (+291 form) was produced with cells of a stable CHO producer clone designated #33-10-29-21, in a 5 liter CelliGen bioreactor in serum free medium (Gibco CHO-A-SFM Cat. no. 95-0091DJ). The crude harvest was clarified by filtration through a 0.8–02 $\mu$ cartridge filter (Gelman Cat. No. CSS92DSCCK) and concentrated 100 fold over a 5-kDa membrane. The +291 form of the r-hsLDLR used for the first immunizations, was purified using a small scale purification process. In this process a DEAE-Sepharose cation exchange column was used, followed by a hydrophobic interaction step on a Butyl-TSK column followed by an HTP column and a size exclusion chromatography (SEC) step on a Sephacryl 100 column. Fraction #27 of the SEC, was chosen, as it contained a specific antiviral activity of 780 units/$\mu$g detected in the antiviral assay described in Example 9 below. The protein in this fraction was identified as r-hsLDLR by N-terminal analysis.

A second batch, of CHO +291 r-hsLDLR was purified and used for boost injections of the mice. It was purified using a refined process having an improved yield which included the following steps: a) clarification and concentration x100 of the crude harvest; b) a HQ POROS anion exchange column, and c) two hydrophobic interaction (HIC) steps: capture on a Butyl-TSK column and flow through a Phenyl 5PW column. The unbound fraction from the last HIC step was dialysed and purified over an HS-POROS cation exchange column. The last step was a Hydroxyapatite (HTP) column. The r-hsLDLR hence obtained was purified to about 90%, eluting as a single major peak in RP-HPLC.

Example 2

Immunization of Mice b 10$\mu$g of the purified r-hsLDLR of fraction #27 of the SEC column of Example 1 above, at a concentration of 100

μg/ml, were homogenised with Complete Freund's Adjuvant (CFA, 50% v/v) and injected into the footpad of each of five 7 week old Balb/C female mice.

Four weeks after the first immunization, the mice were boosted, intramuscular with 10 μg of the same fraction of purified r-hsLDLR, in a 50% (v/v) solution of CFA.

Two weeks after the second injection the mice sera was tested for antibodies to r-hsLDLR, using the direct ELISA described in Example 3 below.

The two mice M-1 and M-2, with the most significant specific immunoreactivity with r-hsLDLR were further boosted, 10 weeks after the second injection, with 10 μg of the purified r-hsLDLR obtained in the refined purification process described in Example 1 above.

The mice were bled 14 weeks later and tested for antibodies to r-hsLDLR. They were then given two additional boosts of 50 μg r-hsLDLR in PBS: the first intraperitoneal and the second, two days later, both intraperitoneal and intravenous.

The mice were bled two weeks after the second injection and the antiserum was tested for anti-r-hsLDLR activity by the direct ELISA of Example 3 below. Each antiserum was serially diluted 1:100–1:32,000 and applied in duplicates to a 96 well plate coated with 10 U/well of r-hsLDLR purified using the refined purification process described in above Example 1. Assay buffer and DMEM+10% HS containing PBS+1% BSA or Gelatin+0.05% Tween 20+0.05% Thimerosal were used as blanks in the first well of each row. Normal Mouse Serum (NMS) was applied in the same dilution range in the last two rows as negative controls. The absorbency of the enzymatic reaction was measured with an ELISA reader at 492 and 405 nm.

The results of this test indicated that sera from mouse M-1 had a higher specific immunoreactivity with r-hsLDLR and was therefore sacrificed and spleen cells were collected for fusion with myeloma cells (Eshhar Z, 1985).

Example 3

Direct ELISA for Antisera Testing and Hybridoma Clones Screening

The direct ELISA for screening for positive antisera was performed as following: 96 wells plates were coated with 100 μl of r-hsLDLR (purified by the refined purification process of example 1) 100 units/ml (10 U/well) in PBS+1% Gelatine (Sigma, Cat. No. G-7765)+0.9 mM $Ca^{+2}$ and 0.5 mM $Mg^{+2}$, pH 5.6, hereinafter referred to as assay buffer, for 90 min. at 37° C. with shaking. The plates were washed six times in PBS+0.05% Tween 20 (Polyoxyethylene-Sorbitan Monolaurate-Sigma P-1379), hereinafter referred to as wash solution.

Anti serum samples from the immunized mice serially diluted 1:100–1:32,000, or supernatant from hybridoma cell cultures were added to the wells and incubated for 90 min. at 37° C., while shaking, followed by six washes in wash solution.

100 μl of Horse Radish Peroxidase (HRP)-APA conjugated goat antibody to mouse Fab (Sigma—Cat. NO. 4601-1) diluted 1:1,200 were added to the wells and incubated for 90 min at 37° C., while shaking, and then washed six times with wash solution.

100 μl of substrate solution (prepared by dissolving one tablet of OPD and one tablet of $H_2O_2$ in 20 ml water) were added to the wells and incubated at RT for 30 min. The enzymatic reaction was stopped by the addition of 100 μl/well of 4N HCl.

The absorbency in the 96 wells plates was read using an ELISA reader at 492 and 405 nm and the results were calculated using the four parametric logistic algorithm, by the MultiCalc software of the PC computer linked to the ELISA reader.

Example 4

Fusion, Hybridoma Preparation, Selection of Clones and Purification of Antibodies from Ascitis Fluids The fusion process and hybridoma cell selection were performed according to the protocols in Eshhar Z, 1985. Briefly, spleen cells from mouse M-1, boosted 2–4 days before fusion, were fused with myeloma cells by a short incubation with PEG. The PEG was first slowly diluted with DMEM and then completely removed by centrifugation. The cells were re-suspended in DMEM-HAT medium, distributed in 96 wells plates at a concentration of about $3.4 \times 10^{-4}$ cells/well and incubated for 10–14 days in an 8% $CO_2$ incubator at 37° C. The medium in all the hybridoma wells was changed to DMEM supplemented with 10% Horse Serum (HS) within 10 days. Hybridoma culture supernatant samples were screened for the presence of Mabs to r-hsLDLR by the direct ELISA described in Example 3 above. Assay buffer and DMEM+10% HS were used as blanks, Mab C7 (commercially available from Amersham) and M-1 mouse antiserum were used as positive controls, while a monoclonal antibody to the soluble p55 TNF receptor was used as a negative control. Cells from wells, in which the presence of antibodies was detected in the culture supernatant, were transferred to 24 well plates and then to 25 $cm^2$ T-flasks. The expanded cultures were monitored for secretion of Mabs to r-hsLDLR. Ampoules of cells from positive cultures were frozen and stored in liquid nitrogen.

A total of approximately 1000 cultures were screened for detecting antibodies to r-hsLDLR. 54 cultures with the highest immuno-activity were re-tested several times. Five cultures (12, 28, 29, 30 and 50) with the highest activity were cloned by limiting dilution in 96 well plates. Supernatants from the growing clones were tested several times for antibodies to r-hsLDLR, by the direct ELISA.

Cells of positive hybridoma clones were grown in tissue culture flasks in DMEM containing 15% horse serum and ampoules were frozen from part of the cultures. In parallel, cells of different hybridoma clones were injected, to 2–4 mice each, to obtain ascitis fluids. Antibodies were purified from ascitis fluid either by ammonium sulphate precipitation or on a protein G column. Briefly 7.5 ml of ascitis fluid were diluted 1:3 in 20 mM Phosphate buffer pH 7 and loaded onto a 5 ml Protein G column (C10/10). The column was washed with 20 mM Phosphate buffer pH 7 and the Mabs were eluted with 100 mM Glycine buffer pH 2.7. The pH of the elution fraction was adjusted to 7–7.5 with 1M Tris buffer pH 9.3.

Example 5

Screening for Pairs of Mabs to be Used in ELISA and Optimisation of the ELISA Parameters The Mabs purified from the ascitis fluids as in example 4 above were used to perform a set of experiments in a matrix format to select the best suitable pair of Mabs to be used as first and second antibodies in the sandwich ELISA for r-hsLDLR described in Example 6 below. Briefly, 96 well plates were coated with ascitis fluids derived from five hybridomas (# 12, 28.28, 29.08, 30 and 50.05) purified either by ammonium sulphate precipitation or on a protein G column. The antibodies were screened using the +291 form as well as the +292 (from amino acid residue Asp +4 to Cys +292) and +331 (from amino acid residue Asp +4 to Cys +331) forms of r-hsLDLR produced in CHO cells, as antigens. One ml of each of the above partially purified Mabs was labelled with biotin for a fast screening of their suitability as second antibodies in a sandwich ELISA. Briefly 1.5 mg of ammonium sulphate precipitation-purified Mabs were adjusted to pH 8.5 with 30 µl of 0.5 M $NaHCO_3$. 0.75 mg of Biotin-OSu N-Hydroxysuccinimido-Biotin (Biotin-OSu, Sigma, Cat. # H1759, from a solution of 5 mg in 200 µl DMSO) were added to the antibody solution and incubated for two hours at room temperature with gentle shaking, followed by an overnight incubation at 2–8° C. The reaction solution was loaded onto a Sephadex G-25M (Pharmacia Cat. #17-0851-01) PD10 column to separate between the biotinylated Mabs and the excess of non-reacted biotin-OSu.

The first preliminary experiments indicated that Mabs 29.08 and 30 produced the highest signal above background, when used as second antibodies in the ELISA.

The reaction of these two clones was tested again as second antibodies with antibodies 12, 28, 29.08 and 50 used for coating of plates. The results of this experiment clearly showed that Mab 28 was the antibody most suitable for coating.

The best results, in terms of signal intensity and specificity, were obtained with Mab 28 used for coating of the microtiter plate, and Mab 29.08, labelled with biotin, as a second antibody. Using these Mabs good results were obtained with all the three forms (+291, +292 and +331) of the r-hsLDLR. With all forms, the absorbency at 492/405 nm was about 1.3 OD.

The three forms of the r-hsLDLR antigen were analysed in serial dilutions in a concentration range of 0.9–1000 ng/ml. A dose response curve was obtained with Mab 28 used for coating and biotinylated Mab 29.08 as a second antibody. This combination gave a linear response at a concentration range of 1–10 ng/ml of r-hsLDLR.

The various parameters that may affect the ELISA test such as concentration of reagents, incubation periods, selection of buffers and plates were optimised by testing the following parameters:

Coating of microtiter plate wells with 5–10 µg/ml of Mab28 in PBS.

Buffer composition:
a) PBS+Tween 20
b) Tris+$Ca^{+2}$+NaCl+Tween 20

Blocking solutions:
a) 1% Gelatine in PBS, 0.05% Tween, 0.005% Thimerosal
b) 1% BSA in PBS, 0.05% Tween, 0.005% Thimerosal
c) 1% FBS in PBS, 0.05% Tween, 0.005% Thimerosal
d) 1% Milk in PBS, 0.05% Tween, 0.005% Thimerosal
e) I Block, Hy Pep and Hy Yeast Second Mab 29.08, labelled with biotin, at concentrations of 1:500, 1:1000, 1:2000, 1:4000, 1:8000, 1:10,000 equivalent to a concentration range of 10.74–0.537 µg/ml.

Extravidin concentrations: 1:500, 1:1000, 1:2000, 1:4000, 1:8000, 1:10,000 equivalent to a concentration range of 4–0.2 µg/ml.

On the basis of these experiments the final procedure for the sandwich ELISA test described in Example 6 below was established.

Example 6

Establishment of a Sandwich ELISA for r-hsLDLR

A sandwich ELISA to the r-hsLDLR was established using Mabs 28 and 29.08. Briefly 96 wells plate were coated with 100 µl of a Protein G purified Mab 28 (5 µg/ml) overnight at 2–8° C. or 3 hrs. at 37° C. The plates were then washed five times with PBS+0.05% Tween 20. The plates were incubated with 200 µl of blocking solution (PBS+ 1%BSA or Gelatin+0.05% Tween 20+Thimerosal 0.05% for one hr at 37° C. or over night at 4° C. and washed five times with PBS+0.05% Tween 20. 100 µl of samples or of calibration curve antigen (CHO +291 r-hsLDLR, 0.5–32 ng/ml diluted in blocking solution), were added to the wells and incubated for 90 min at 37° C., with shaking. The plates were then washed five times with PBS+0.05% Tween 20.

100 µl/well biotinylated Mab 29.08 (0.67 µg/ml) in blocking solution were added, and incubated with shaking for one hour at 37° C. The plates were washed five times with PBS+0.05% Tween 20. 100 µl of a commercial extravidin— peroxidase conjugate, (ExtrAvidin TM-Peroxidase BioMakor, Cat.# 0645-1) diluted 1:10,000 were added to the wells and incubated with shaking for one hour at 37° C. The plates were then washed five times with PBS+0.05% Tween 20. 125 µl of the abovementioned substrate solution were added to each well and incubated for about 10 minutes until the colour developed to the desired intensity. The reaction was stopped by adding 125 µl of 4N HCL. The absorbency in the 96 wells plates was read using an ELISA reader at 492 and 405 nm wavelengths and the results were calculated by the MultiCalc software of the PC computer linked to the ELISA reader.

Example 7

Monoclonal Antibodies Isotype

The monoclonal antibodies Ig isotype was determined using a commercial isotyping kit (PharMingen International) according to the manufacturer's assay procedure. Clones 12.6, 28, 29.8 and 30 were identified as $IgG_1$, whereas clone 50.30 was found to be of the IgM class.

Example 8

SDS-PAGE Western Blot Analysis

The +291 form of purified r-hsLDLR and the native LDLR purified from human urine were analysed by western blot analysis with the monoclonal antibodies developed to the r-hsLDLR. Briefly a 12% SDS Poly Acrylamide gel was loaded with 100 ng/lane of the CHO +291 form of r-hsLDLR, or native urinary hsLDLR or TBP-1 crude harvest (as negative control) under reducing conditions (40 mM DTT). One lane was loaded with Low Molecular Weight Markers (LMW). This set of samples was run five times. The proteins separated on the gels were transferred by electro-elution to nitrocellulose membranes. The membranes were incubated in PBS containing 10% low-fat milk, 0. 1% Tween 20, for 16 hr. The membranes were cut into strips and each strip was incubated for 2 hours at room temperature with one of the five selected Mabs: 12.6, 30, 50.30, 28 or 29.08 (ascitis fluid diluted 1:4000).

Membrane strips were washed with PBS containing 0.1% Tween 20 (3×15 min) and incubated for one hour with the second antibody—goat anti-mouse conjugated to horseradish peroxidase-alkaline phosphatase (diluted 1:10.000, BioMakor) for 2 hours at room temperature.

The strips were washed with PBS containing 0.1% Tween 20 (3×15 min). The positive bands were detected by enhanced chemiluminescence (ECL, Amersham).

Figure 1:
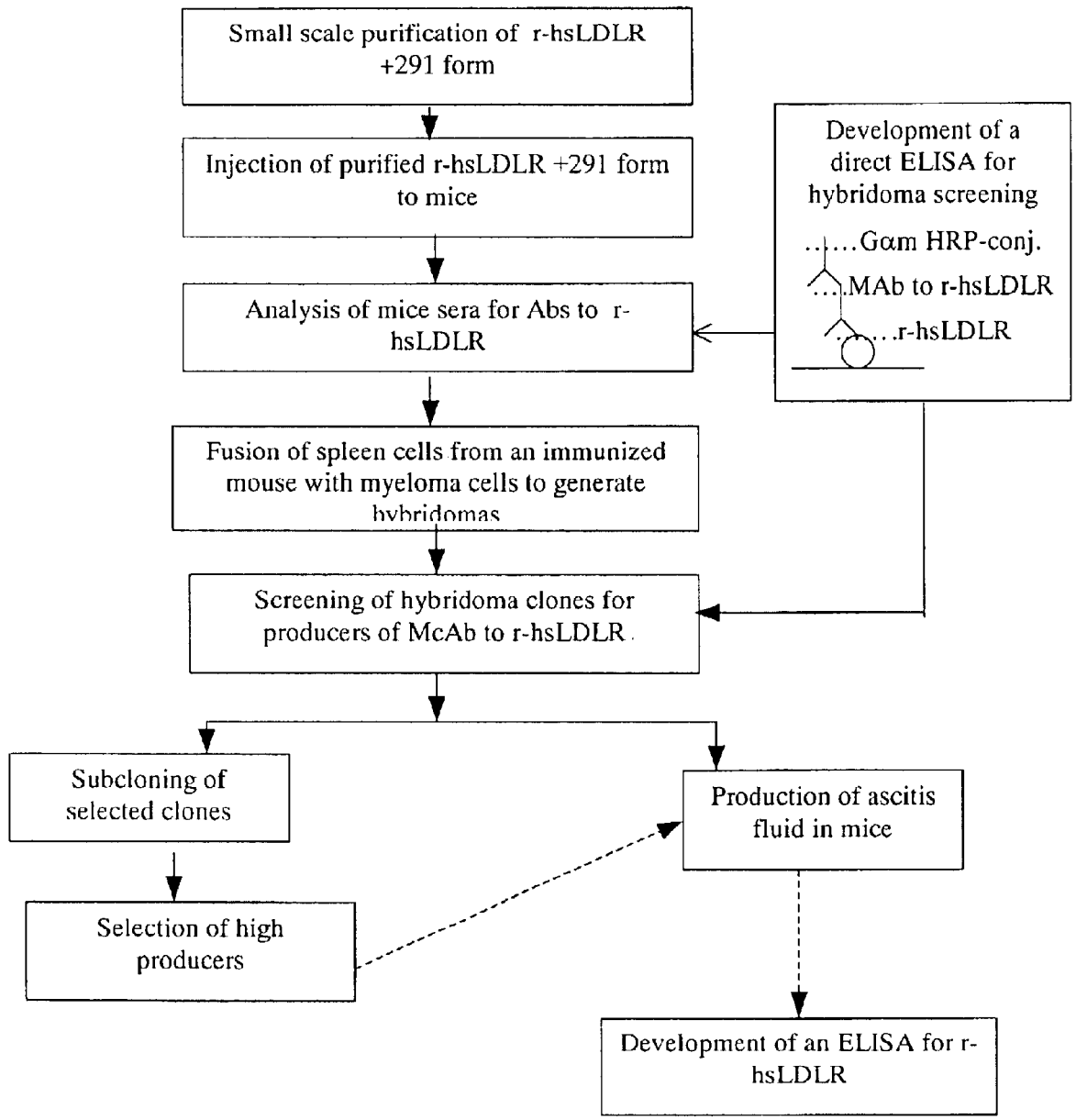
FIG. 1 shows a flow chart depicting the development of monoclonal antibodies to r-hsLDLR.
Figure 2:
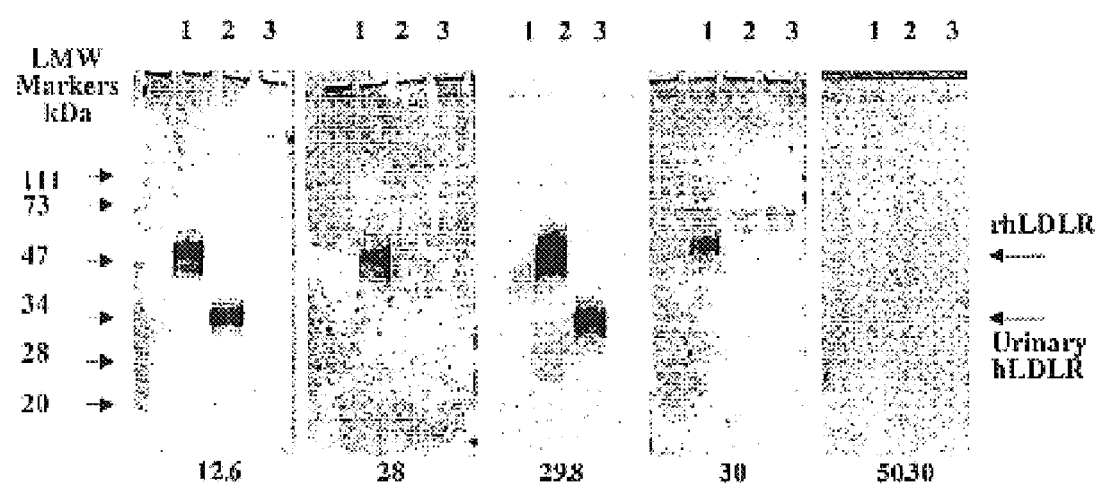
FIG. 2 shows a Western blot analysis of the +291 form of r-hsLDLR in lane 1, the urinary hsLDLR in lane 2 and recombinant human p55 TNF receptor as a negative control (r-hTBP-1) in lane 3, with the monoclonal antibodies indicated beneath each strip. The arrows to the left of the figure indicate the position of the molecular weight markers and the arrows to the right of the figure point to the position of the hsLDLR form indicated above each arrow.

Monoclonal antibodies #12.6 and #29.8 recognised both the urinary as well as the +291 form of the purified r-hsLDLR in western blot analysis (FIG. 2). Mabs 28 and 30 recognised the +291 form of the purified r-hsLDLR.

Example 9

Inhibition of r-hsLDLR Antiviral Activity by Monoclonal Antibodies

Mabs which specifically reacted with r-hsLDLR were tested for their ability to block the antiviral activity of r-hsLDLR (+291 form) in-vitro, using a cytopathic effect (CPE) inhibition assay in a VSV/WISH system.

WISH cells (of human amnion origin) were cultured in MEM supplemented with 10% FBS and 4 mM glutamine in a 37° C., 5% $CO_2$ incubator. Exponentially growing cells were seeded in 96-well tissue culture plates, at a density of 40,000 cells/well twenty-four hours before initiation of the assay. Samples to be tested and the standard were diluted and dispensed into the cells' containing wells. VSV was immediately added to the wells, at a multiplicity of Infection (MOI) of 0.5 pfu/cell. The plates were incubated 16–18 hours at 37° C. and were then washed with ethanol. The monolayer of surviving cells was viewed by Gram Crystal Violet stain. Quantitation of the cytopathic effect relative to the standard was performed by plotting the colour density versus standard concentration.

For analysing the neutralising effect of the antibodies, r-hsLDLR was pre-incubated for 30 min. at 37° C., with increasing concentrations of ascitis fluid of the Mab tested. These solutions were then added to cultures of WISH cells in 96 microtiter plates, followed by the addition of vesicular stomatitis virus (VSV). After 18 hours incubation, the VSV mediated cell lysis was determined by staining of the remaining cells with crystal violet. Semi-quantitation of the cytopathic effect relative to the standard was performed by plotting the colour intensity (determined by an ELISA reader) versus standard concentration.

The effect of the Mabs was tested with increasing concentrations of r-hsLDLR. As shown in Table 1 two Mabs (12.6 and 50.30) were found to display neutralising activity.

In the experiment shown in Table 1, the inhibitory effect of the two Mabs was tested at a 1:40 dilution of the ascitis fluids. At this dilution, Mab 12.6 displayed somewhat higher activity than to Mab 50.30. This may result from the properties of the Mabs, as well as from differences in their concentration in the ascitic fluid.

The inhibitory effect of the Mabs could be overcome by increasing r-hsLDLR relative to Mabs concentration. In fact at r-hsLDLR concentrations of 62.5 U/ml, neither Mab had any effect on r-hsLDLR activity at the antibody concentration analysed.

TABLE 1

Inhibition of r-hsLDLR antiviral activity by clones 12.6 and 50.30[1]

| VSV/Mab | LDLR Concentration (U/ml) | | | |
|---|---|---|---|---|
| | 0 | 2.5 | 12.5 | 62.5 |
| −VSV | 1.5 | 1.2 | 1.6 | 1.5 |
| +VSV | (0.25) | 1 | 7 (1.7) | 1.7 |
| +VSV + Clone 50.30 | 6 (0.4) | 0.88 | (1.25) | 1.62 |
| +VSV + Clone 12.6 | 5 (0.5) | 0.77 | 7 (0.7) | 1.67 |

[1]Inhibition of r-hsLDLR antiviral activity against VSV mediated cell lysis of WISH cells. The inhibitory effect of the Mabs was determined at a 1:40 dilution of the ascitis fluid. The number of viable cells is represented in the table in OD values. Numbers in brackets represent a repetition performed at the 0 and 12.5 U/ml LDLR concentrations.

Inhibition of the antiviral activity of r-hsLDLR was determined using increasing concentrations of Mabs 12.6 and 50.30. Mab 12.6, inhibited the antiviral activity of r-hsLDLR, by ~60% at a 1:40 dilution (of the ascitis fluid) and by ~35% at a 1:20,500 dilution. Clone 50.30 inhibited r-hsLDLR activity by ~45% at the 1:40 dilution and by ~15% at 1:20,500 dilution.

The dose response curve, obtained with both Mabs, and the observation that their inhibitory effect was impaired by excess r-hsLDLR, suggest that the Mabs exert their effect by binding to r-hsLDLR.

Example 10

Inhibition of HCV Replication by Monoclonal Antibodies

Mabs specific for r-hsLDLR were tested for their ability to inhibit HCV replication in human hepatocytes in primary culture. FT167 cell culture was derived from a 57 year old male patient requiring lobectomy resection for medical purposes (metastasis of a colon tumor, right lobe).

Primary cultures of human hepatocytes were prepared by the two steps collagenase perfusion method (Maurel P. Adv.Drug Del.Rev. 22:105–132 (1996), Pichard L. et al. Mol. Pharmacol. 41:1047–1055(1992), Ferrini JB. Et al. Chem-Biol Interactions 107:31–45 (1997)). The viability of the cells before plating was determined using trypan blue exclusion test. Four million cells in 3 ml of culture medium were placed into 60-mm plastic dishes precoated with collagen The long-term serum-free culture medium consisted of Williams'E, supplemented as published (Lanford R. et al. In Vitro Cell Dev. Biol.25:174–182 (1989)). This medium was subsequently renewed every 48 hours. Cultures were maintained at 37° C. in a humid atmosphere of air and 5% carbon dioxide. Under these culture conditions, human hepatocytes retain their differentiated phenotype for at least 35 days (Ferrini J B. Et al. Chem-Biol Interactions 107:31–45 (1997)) and are sensitive to HCV Infection and permissive to the viral genome replication (Fournier C. et al. J. Gen Virol. 79:2367–2374 (1998)).

HCV-positive serum sample: A bank of human sera from patients tested anti-HCV antibody-positive by the EIA HCV 3.0 and Chiron RIBA HCV 3.0 SIA has been established. None of these patients was co-Infected with HBV or HIV. In each serum sample HCV RNA was quantitated by the Roche monitor and genotyped by a line probe assay (Inno-Lipa HCV II, Innogenetics). Serum samples were stored at −80° C., in small aliquots in order to avoid freezing-thawing cycles. In these experiments the sample S42 (genotype 1b; viral load: 410 000 copies/ml) was used.

For infection and subsequent treatments, hepatocyte cultures were transferred under sterile conditions to a P3-laboratory (high confinement for human-IFNectious micro-organisms). Three days after plating, when the cells had recovered from the traumatism of isolation, in vitro infection of hepatocytes was performed by an overnight incubation with 25 µL of HCV-positive serum sample (S42) in 3 mL of medium. After infection, cells were washed three times with 3 mL of fresh medium and the culture was continued under normal conditions in the long-term culture medium.

Cells were treated with 3 different Mabs against r-hsLDLR, Mab12.6, Mab28 and Mab29.8. Thirty minutes before infection, cells were exposed to 2 or 8 µg/ml of the different Mabs. Then cells were infected as described above.

Control cultures were infected under similar conditions but in the absence of antiviral treatment. In parallel experiments, the same cultures were treated with 5000 U/mL IFNα, under similar conditions for comparison (IFNα strongly inhibits HCV replication in the cells ref). All treatments were carried out in duplicate.

At day 5 post-Infection, the medium was removed and the cultures washed 3 times with cold phosphate-buffered saline. RNA was purified from $4 \times 10^6$ hepatocytes using a guanidinium isothiocyanate-acid phenol extraction procedure (Chomczynski P N. And Sacchi N. Analyt. Biochem. 162:156–159 (1987)). The precipitated RNA was dissolved in 50 µL of diethylpyrocarbonate (DEPC)-treated water and quantified. One µg of cellular RNA was analyzed in the strand-specific rTth RT-PCR assay.

To avoid possible contamination, the strand-specific RT-PCR assay was carried out sequentially using the three different rooms: a pre-PCR room, a PCR room and a post-PCR room. RNA dissolved in 10 µl of DEPC-treated water was covered with mineral oil and heated at 95° C. for 1 min. The temperature was lowered to 70° C. and 10 µl of preheated cDNA reaction mixture. was added. The temperature was then dropped to 60° C. for 2 min for annealing and the cDNA reaction was performed for 20 min at 70° C. using the rTth DNA polymerase (Perkin-Elmer). The temperature was maintained at 70° C. while 40 µl of prewarmed buffer containing EGTA as chelator of $Mn^{2+}$ was added to suppress the rTth RT activity. Reaction tubes were held at 70° C. while 40 µl of prewarmed PCR mixture was added. The PCR conditions, performed on Gene Amp® PCR-System 9600 (Perkin-Elmer), consisted of an initial cycle at 94° C. for 1 min, 50 cycles at 94° C. for 15 sec, 58° C. for 30 sec, 72° C. for 30 sec and a final extension step at 72° C. for 7 min. For positive strand HCV RNA assay, the nucleotide sequence of the reverse primer P3 is: 5'-TGG/ATGCACGGTCTACGAGACCTC-3' (SEQ ID NO:1), (nt 342–320) and that of the forward primer P4 is: 5'-CACTCCCCTGTGAGGAACT-3' (SEQ ID NO:2), (nt: 38–56), (Laskus T. et al. J. Gen. Virol. 78:2747–2750 (1997)). The same primers were used in reverse order to detect the negative strand. One-tenth of the amplified product was analyzed by gel electrophoresis on agarose (2%), followed by coloration with BET and photography under UV light. In all series of experiments, dilutions of synthetic HCV RNA (+) and (-) strands were made and 1 µg of total liver RNA was added to mimic the conditions for analysis of cultured hepatocytes. These mixtures were used as positive controls for RT-PCR assay and analysis.

FIG. 3 shows that the production of the HCV negative strand, in the precence of the Mabs againt LDLr, was fully inhibited in culture FT167. Therefore the replication of the viral genome was strongly inhibited. The results were consistent with the view that the LDLR might be a receptor for HCV.

Example 11

Production of Chimeric Antibodies to LDLR mRNA is purified from a hybridoma line producing mAb specific for LDLR.

Specific cDNA is synthesized with olygonucleotides complementary to the 5∝ end of the exon CH1 from the heavy chain variable domain (oligo 1) and from the 5' of the Cκhexon of the light chain variable domain (oligo 2) using the purified mRNA as the template.

Two cDNAs are obtained one of which encode the variable region (specific for LDLR) of the heavy chain, and the other the variable region (specific for the LDLR) of the light chain. The cDNAs are cloned and sequenced.

For the construction of the chimeric heavy chain, the variable region of a cloned human Ig heavy chain gene is exchanged (using genetic manipulations) for the cloned DNA encoding the mouse variable domain (specific for LDLR) of the heavy chain. The genetic manipulations include excition of the variable region from the human Ig, using specific restriction enzymes and ligation of the mouse variable region. The same procedure is performed to obtain the chimeric light chain.

Two mammalian expression plasmids are constructed, one including the chimeric heavy chain gene and the other including the chimeric light chain gene. Both vectors are used to cotransfect the hybridoma cell line (SP6).

The production of LDLR specific Ig is tested by ELISA or western blots using culture soup of transfectant cells as secondary antibody. The affinity of the chimeric antibody to its ligand is monitored by Biacore.

Example 12

Preparation of Transgenic Mice that are Engineered to Contain Human Immunoglobulin Gene Loci (Xenomice) and Preparation of Human mAb against hLDLR Xenomice preparation is described in WO 98/24893 and Mendez M, J. et al Nature genetics 15:146–56(1997).

Human-yeast artificial chromosome (YAC) libraries are screened for YACs containing the human heavy chain variable region (about 1000 kb) (YAC cloning method is the method of choice when inserts sizes bigger of 100 kb are required).

The YACs are characterized by Southern blot analysis and by Pulse Field Electrophoresis (PFGE). The YACs should include the Cμ Cδ, Dh and Vh regions in germ line configuration.

Through utilization of the overlapping sequences contained in the YACs, the YACs are recombined in yeast by stepwise recombination strategy. Prior to recombination the 3' end YAC (with the V region) is ligated to HPRT selectable marker. The structure of recombined YAC is confirmed by PFGE and Southern blot analysis (presence of the human heavy chain locus from C region to Vh region in germline configuration).

The YAC acentric arm is targeted with a vector bearing the complete γ2 constant region, mouse enhancer, neomycin resistance gene, to yield the final heavy chain containing the whole variable region i.e. 82 Vh genes, 6 Jh genes and 3 different constant regions Cμ Cδ Cγ with their corresponding regulatory sequences. This YAC is designated yH2. This construct is used for the production of the Xenomouse.

A similar strategy to the one used above is utilized for the reconstruction of the kappa loci, only that: neomycin selection marker is ligated to the reconstructed YAC containing the whole kappa loci. This YAC is designated yK2.

YACs containing the yH2 are introduced into ES cell via fusion of YAC containing yeast spheroplast with HPRT deficient E14.TG3B mouse ES cells. HPRT positive cells are selected. Positive clones are propagated and analyzed by Southern blots and by CHEF blot analysis. Clones containing the intact yH2 YAC are selected.

Introduction and selection of yK2 YAC in ES cells is performed similarly as described for yH2 YAC.

YH2 containing ES cells are microinjected into mouse C57BL/6J blastocytes. The chimeric males produced are evaluated for germ line transmission to offspring.

yH2 and or yK2-transgenic mice are bred with DI mice (homozygous for gene targeted-inactivated mouse heavy and kappa chain loci). Each of the yH2;DI transgenic strains are bred with yK2;DI transgenic strain to generate Xenomouse strains.

Reconstitution of B-cell development and antibody production in Xenomouse is evaluated by flow cytometry and ELISA.

The immunization of xenomouse is performed as described in example 2.

The methods for the hybridoma preparation and screening of positive clones are similar to those described in examples 3 and 4.

Hybridoma clones 12.6, 28, 29.8, 30 and 50.30 were deposited at the Collection Nationale de Culture de Microorganismes (CNCM), Institut Pasteur, 28, Rue du Docteur Roux, F-75724, Paris, CEDEX 15, France, under the Budapest Treaty and were accorded deposit Nos. I-2390, I-2391, I-2392, I-2393 and I-2394, respectively. The above deposits were made on Mar. 10, 2000.

References

Agnello, V., Abel, G., Elfahal, M., Knight, G. B., and Zhang, Q. X. (1999). "lepatitis C virus and other flaviviridae viruses enter cells via low density lipoprotein receptor [In Process Citation]." *Proc Natl Acad Sci USA*, 96(22), 12766–71.

Beisiegel, U., Schneider, W. J., Goldstein, J. L., Anderson, R. G., and Brown, M. S. (1981). "Monoclonal antibodies to the low density lipoprotein receptor as probes for study of receptor-mediated endocytosis and the genetics of familial hypercholesterolemia." *J Biol Chem*, 256(22), 11923–31.

Bieri, S., Djordjevic, J. T., Daly, N. L., Smith, R., and Kroon, P. A. (1995). "Disulfide bridges of a cysteine-rich repeat of the LDL receptor ligand-binding domain." *Biochemistry*, 34(40), 13059–65.

Brown, M. S., and Goldstein, J. L. (1976). "Familial hypercholesterolemia: A genetic defect in the low-density lipoprotein receptor." *N Engl J Med*, 294(25), 1386–90.

Brown, M. S., and Goldstein, J. L. (1986). "A receptor-mediated pathway for cholesterol homeostasis." *Science*, 232(4746), 34–47.

Chomczynski, P. N., And Sacchi, N. (1987). "Single-step method of RNA isolation by acid guanidinium thiocyanate-phenol-chloroform extraction". Analyt. Biochem. 162:156–9.

Eshhar Z, 1985 "Monoclonal Antibody Strategy and Techniques" in "Hybridoma technology in the bioscience and medicine", Edited by Timothy A. Springer (Plenum Publishing Corporation, 1985; Chapter 1)

Fischer, D. G., Tal, N., Novick, D., Barak, S., and Rubinstein, M. (1993). "An antiviral soluble form of the LDL receptor induced by interferon". *Science*, 262(5131), 250–3.

Fischer, D. G., Novick, D., Cohen, B, Rubinstein, M. (1994). "Isolation and characterization of a soluble form of the LDL receptor, an interferon-induced antiviral protein". Proc Soc Exp Biol Med 206(3),228–32.

Ferrini, J. B., Pichard, L., Domergue, J., and Maurel, P. (1997). "Long-term primary cultures of adult human hepatocytes". Chem-Biol Interactions 107:31–45.

Fournier, C., Sureau, C., Coste, J., Ducos, J., Pageaux, G., Larrey, D., Domergue, J., and Maurel, P. (1998). "In vitro infection of adult normal human hepatocytes in primary culture by hepatitis C virus". J. Gen Virol. 79:2367–74.

Goldstein, J. L., Anderson, R. G., and Brown, M. S. (1979). "Coated pits, coated vesicles, and receptor-mediated endocytosis." *Nature*, 279(5715), 679–85.

Goldstein, J. L., Dana, S. E., Brunschede, G. Y., and Brown, M. S. (1975). "Genetic heterogeneity in familial hypercholesterolemia: evidence for two different mutations affecting functions of low-density lipoprotein receptor." *Proc Natl Acad Sci USA*, 72(3), 1092–6.

Lanford R. E., Carey, K. D., Estlack, L. E., Smith, G. C., and Hay, R. V. (1989) "Analysis of plasma protein and lipoprotein synthesis in long-term primary cultures of baboon hepatocytes maintained in serum-free medium" In Vitro Cell Dev. Biol. 25:174–82.

Laskus T., Radkowski, M., Wang, L. F., Cianciara, J., Vargas, H., and Rakela, J. (1997). "Hepatitis C virus negative strand RNA is not detected in peripheral blood mononuclear cells and viral sequences are identical to those in serum: a case against extrahepatic replication". J. Gen. Virol. 78:2747–50.

Maurel P. (1996) "The use of adult human hepatocytes in primary culture and other in vitro systems to investigate drug metabolism in man". Adv.Drug Del.Rev. 22:105–132

Mendez, M. M., Green, L. L., Corvalan, J. R. F., Jia X-C., Maynard-Currie, E. E., Yang, X-D., Gallo, M. L., Louie, D. M., Lee, D. V., Erickson, K. L., Luna, J., Roy, C. M-N., Abderrahim, H., Kirshenbaum, F., Noguchi, M., Smith, D. M., Fukushima, A., Hales, J. F., Finer, M. H., Davis, C. G., Zsebo, K. M. and Jakobovits, A. (1997). "Functional transplant of megabase human immunoglobulin loci recapitulates human antibody response in mice". Nature Genetics, 15, 146–56.

Pichard, L., Fabre, I., Daujat, M., Domergue, J., Joyeux, H., and Maurel, P. (1992). "Effect of corticosteroids on the expression of cytochromes P450 and on cyclosporin A oxidase activity in primary cultures of human hepatocytes". Mol. Pharmacol. 41:1047–55.

Riachmann, L., Clark, M., Waldmann, H., and Winter, G. (1988). "Reshaping human antibodies for therapy." Nature, 332, 323–27.

Sudhof, T. C., Goldstein, J. L., Brown, M. S., and Russell, D. W. (1985). "The LDL receptor gene: a mosaic of exons shared with different proteins." *Science*, 228(4701), 815–22.

Urlaub, G. and Chasin, L. A. (1980) Isolation of Chinese Hamster Cell Mutants Deficient in Dihydrofolate Reductase Activity. Proc. Natl. Acad. Sci. USA 77: 4216–4220.

What is claimed is:

1. A monoclonal antibody expressed by hybridoma clone 12.6 deposited at the CNCM under No.1-2390.

2. A monoclonal expressed by hybridoma clone 28 deposited at the CNCM under No. I-2391.

3. A monoclonal antibody expressed by hybridoma clone 29.8 deposited at the CNCM under No. I-2392.

4. A monoclonal antibody expressed by hybridoma clone 30 deposited at the CNCM under No. I-2393.

5. A monoclonal antibody expressed by hybridoma clone 50.30 deposited at the CNCM under No. I-2394.

6. A hybridoma clone 12.6 deposited at the CNCM under No.1-2390.

7. A hybridoma clone 28 deposited at the CNCM under No.1-2391.

8. A hybridoma clone 29.8 deposited at the CNCM under No.1-2392.

9. A hybridoma clone 30 deposited at the CNCM under No.1-2393.

10. A hybridoma clone 50.30 deposited at the CNCM under No. I-2394.

11. A method for purifying human low-density receptor (LDLR) which comprises contacting a material containing crude human LDLR with the monoclonal antibody according to any one of claims 1–5 to affinity purify human LDLR.

12. A method for neutralizing an antiviral biological activity of recombinant human soluble low-density lipoprotein receptor (r-hsLDLR) comprising contacting r-hsLDLR with the monoclonal antibody of claim 1 or 5 to neutralize an antiviral biological activity of r-hsLDLR.

13. A method for inhibiting replication of hepatitis C virus, comprising contacting cells with the monoclonal antibody of claim 1, 2 or 3 prior to infection by hepatitis C virus to inhibit replication of hepatitis C in the cells.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial
<220> FEATURE:
<223> OTHER INFORMATION: Synthetic

<400> SEQUENCE: 1
tggtgcacgg tctacgagac ctc                                            23

<210> SEQ ID NO 2
<211> LENGTH: 19
<212> TYPE: DNA
<213> ORGANISM: Artificial
<220> FEATURE:
<223> OTHER INFORMATION: Synthetic

<400> SEQUENCE: 2
cactcccctg tgaggaact                                                 19